United States Patent [19]
Theeuwes et al.

[11] 4,305,927
[45] Dec. 15, 1981

[54] METHOD FOR THE MANAGEMENT OF INTRAOCULAR PRESSURE

[75] Inventors: Felix Theeuwes; William F. Bayne, both of Los Altos, Calif.

[73] Assignee: ALZA Corporation, Palo Alto, Calif.

[21] Appl. No.: 119,944

[22] Filed: Feb. 8, 1980

Related U.S. Application Data

[63] Continuation-in-part of Ser. No. 9,402, Feb. 5, 1979, abandoned, which is a continuation-in-part of Ser. No. 852,904, Nov. 18, 1977, abandoned, which is a continuation-in-part of Ser. No. 675,186, Apr. 8, 1976, abandoned.

[51] Int. Cl.$^3$ ...................... A61K 9/44; A61K 31/425
[52] U.S. Cl. ........................................ 424/15; 424/80; 424/270
[58] Field of Search ............................ 424/80, 15, 270

[56] References Cited

U.S. PATENT DOCUMENTS 3,916,899  11/1975  Theeuwes et al. .................. 128/260

OTHER PUBLICATIONS

Physicians Desk Reference, (PDR), 22nd ed., pp. 736–738, (1968).

Primary Examiner—Leonard Schenkman
Attorney, Agent, or Firm—Paul L. Sabatine; Edward L. Mandell

[57] ABSTRACT

A method for the management of intraocular pressure and for lessening the incidence of side effects associated therewith is disclosed. The method comprises administering continuously controlled low dosage amounts of acetazolamide to produce both a lessening of the side effects and lowering of the intraocular pressure.

8 Claims, 18 Drawing Figures

METHOD FOR THE MANAGEMENT OF INTRAOCULAR PRESSURE

CROSS-REFERENCE TO RELATED APPLICATION

This application is a continuation-in-part of U.S. application Ser. No. 9,402 filed on Feb. 5, 1979, which application is a continuation-in-part of U.S. patent application Ser. No. 852,904 filed on Nov. 18, 1977, which application is a continuation-in-part of U.S. application Ser. No. 675,186 filed on Apr. 8, 1976 and all now abandoned. This application and applications Ser. Nos. 9,402, 852,904 and 675,186 are all assigned to the ALZA Corporation of Palo Alto, Calif. Applications Ser. Nos. 9,402, 852,904 and 675,186 are incorporated herein by reference, and benefit of its filing date is claimed.

BACKGROUND OF THE INVENTION

1. Field of the Invention

This invention pertains to ocular pharmacology. More particularly, the invention relates to a method for unexpectedly lessening the incidence of side effects associated with lowering intraocular pressure by administering continuously acetazolamide in controlled, unexpected low dosage amounts to produce both the lessening of side effects and a lowered intraocular pressure. Specifically, the invention pertains to the management of intraocular pressure associated with glaucoma by an improved therapeutic program.

2. Description of the Prior Art

Acetazolamide, or 5-acetamido-1,3,4-thiadiazole-2-sulfonamide, and its therapeutically acceptable salts, is a well-known drug used for lowering elevated ocular pressure. Generically, acetazolamide is an enzyme inhibitor that acts on carbonic anhydrase, the enzyme which catalyzes the reversible reaction involving the hydration of carbon dioxide and the dehydration of carbonic acid. Specifically, in the eye, acetazolamide's inhibiting action decreases the secretion of aqueous humor and results in a lowering in intraocular pressure. This reaction is desirable in the management of glaucoma, a physical condition characterized by increased intraocular pressure due to a restricted outflow of the aqueous homor through the aqueous veins and Schlemm's canal. Acetazolamide is particularly indicated for treating primary glaucoma including narrow-angle or acute and wide-angle or chronic simple glaucoma, secondary glaucoma, and preoperatively in acute-angle closure glaucoma where a delay of surgery is desired in order to lower intraocular tension. The preparation of acetazolamide is reported in *J. Am. Chem. Soc.*, Volume 72, pages 4890 to 4892, 1950, in U.S. Pat. Nos. 2,554,816 and 2,980,679. The pharmacology of acetazolamide and the disease glaucoma are described in *The Pharmacological Basis of Therapeutics*, 4th Edition, by Goodman and Gilman, pages 458 to 459, and pages 851 to 852, 1970, published by the Macmillan Company, New York; and in *General Ophthalmology*, by Vaughn and Asbury, pages 192 to 209, 1974, published by Lange Medical Publications, Los Altos, Calif.

Presently, the drug acetazolamide is administered for the above conditions in two different oral dosage forms. In one form, acetazolamide is formulated into conventional, standard pharmaceutical tablets, hereafter called the tablet. The tablets are not a sustained dosage form, and they do not provide for the continuous administration of acetazolamide. The tablets contain 125 mg or 250 mg, usually administered at the recommended dose of up to 1 gm per day, to provide both instant acetazolamide and short-term action for reducing aqueous humor secretion at a declining rate of 8 to 12 hours. In the other form, acetazolamide is formulated into sustained release dosage form, hereafter called the sustained release form. The sustained release form contains 500 mg of acetazolamide, and it has a recommended dose of 2 times a day to provide prolonged action for reducing aqueous humor secretion for 18 to 24 hours. The mechanism of sustained release is obtained by progressive variation in the size of coated granules of the drug and in the proportionate quantities of the various sized granules present in the sustained release form, as reported in *Am. J. of Opth.*, Volume 55, pages 323 to 327, 1963. While these prior art forms of administration enjoy wide use for treating glaucoma, serious shortcomings are associated with their use. For example, the tablets dissolve too quickly, and they release their acetazolamide instantaneously; and the sustained release form can exhibit a release rate curve showing exponential decay as a function of time, a rate which is further highly dependent on pH, thereby making it difficult to know how much drug is administered at a given time. The use of the tablet and the sustained release form, can also lead to adverse reactions or side effects, including drowsiness, paresthesias and confusion. These side effects are described in the *Medical Dictionary*, by Stedman, pages 355, 358, 482 and 1180, published in 1966 by the Williams and Wilkins Co., Baltimore, Md. The common and wide use of acetazolamide with its accompanying high incidence of adverse reactions creates an immediate and pressing need for a new and useful therapeutic method of administering acetazolamide, which method produces the desired pharmaceutical and physiological results while substantially lessening the unwanted reactions associated with modes of acetazolamide administration used by the prior art.

SUMMARY OF THE INVENTION

Accordingly, it is an immediate object of this invention to provide a novel therapeutic method for administering acetazolamide which method substantially lessens the incidence of side effects or the adverse reactions associated with the prior art methods of administration.

Another object of the invention is to provide a new and useful delivery rate profile for administering acetazolamide for the management of glaucoma characterized by a lowering of intraocular pressure, which profile lowers intraocular pressure while concomitantly reducing the incidence of side effects usually accompanying acetazolamide administration.

Another object of the invention concerns a method for the management of ocular hypertension comprising administering acetazolamide and its salts at a given mass per unit time released as a function of time to produce a hypotensive effect. The method achieves the hypotensive result without excessive side effects.

Another object of the invention is to provide for the management of glaucoma by administering acetazolamide at a continuous rate and at up to one-half the amount administered by the prior art sustained release form while still lowering the intraocular pressure to within the average normal range.

Yet another object of this invention is to provide a therapeutic program for administering acetazolamide at a lower amount then the amount presently indicated by the prior art, while simultaneously substantially reducing the intraocular pressure to levels heretofore obtained at higher dose amounts.

Yet still another object of the invention is to administer acetazolamide in lower dose for producing lower blood concentrations of acetazolamide while simultaneously reducing intraocular pressure to levels obtained with higher doses and higher blood concentrations of acetazolamide.

Still another object of the invention pertains to a method comprising administering acetazolamide from an osmotic therapeutic system in a controlled and continuous low dosage amount per unit time to cause a lowering of intraocular pressure and a lessening of side effects.

Yet still another object of the invention is to provide a method for controlled inhibition of the enzyme carbonic anhydrase as seen by a decreased intraocular pressure which decrease is coextensive with a significant lowering of unwanted side effects that usually accompany the pharmacological inhibition of the enzyme.

Still a further object of the invention is to provide a method of orally administering acetazolamide to systemically control its plasma level for achieving a controlled lowering of intraocular pressure while at the same time avoiding undesirable excessive toxic levels and lessening the incidence of side effects.

These and other objects of the invention will become more apparent from a consideration of the accompanying detailed disclosure, the figures, and the appended claims.

DETAILED DESCRIPTION OF THE INVENTION

This invention resides in the discovery that acetazolamide can be administered in unexpectedly lower, controlled and continuous dosage amounts per unit time to lessen the incidence of side effects, while effectively lowering intraocular pressure. The method comprises administering acetazolamide and its salts, from an osmotic drug delivery system, to the gastrointestinal tract in a controlled and continuous effective amount at a substantially zero order rate over a major time interval of a prolonged period according to a precise dosage program. The purpose of the dosage program is to administer acetazolamide at a substantially constant rate in an amount required for producing effective blood plasma levels for lowering intraocular pressure while additionally minimizing excessively high levels of the side effects commonly associated with the use of acetazolamide. The amount of acetazolamide administered in the dosage program is an effective amount up to 20 mg per hour for producing a lessening of side effects and a lowering of intraocular pressure, and it is in a preferred range of an effective amount usually from about 10 mg to 20 mg per hour over a prolonged period up to 12 hours. A presently preferred drug delivery program comprises administering 10 to 20 mg per hour during the first 6 hours, followed by from 10 to 15 mg per hour over the next 3 hours, and then 2 to 7 mg per hour at substantially non-variable rates of administration over the next 3 hours for 40 kg to 120 kg adult male or female patient. The acetazolamide in a presently preferred embodiment was administered continuously at these described rates over a prolonged period up to 15 hours by using an osmotic drug delivery system manufactured in the form of an oral osmotic drug delivery device as described in U.S. Pat. Nos. 3,854,770 and 3,916,899. These patents are assigned to the ALZA Corporation of Palo Alto, Calif., the assignee of this application. In U.S. Pat. No. 3,916,899 acetazolamide is disclosed as a drug that can be released by the device. The recommended dose at the time filing and issuance of said patent was for a sustained release non-osmotic dosage form, a dose of 500 mg two times a day for a total dose of 1000 mg per day; as reported in *Physician Desk Refer-*

*ence,* 22nd Edition, pages 736 to 738, 1968, published by Medical Economics Company, Oradell, N. J. The release of acetazolamide for the osmotic devices made for use herein occurs at a rate independent of pH of the environment of use, and substantially free of any stirring rate dependency.

Figure 1:
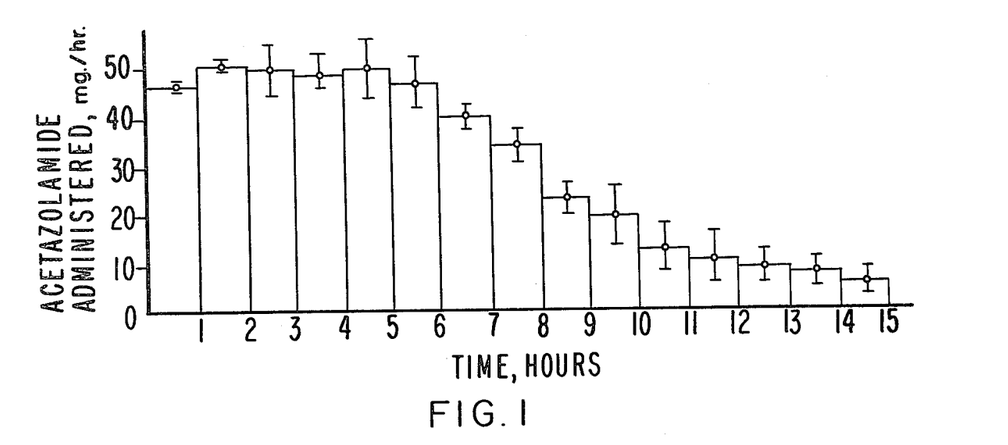
FIG. 1 illustrates the average rate of release for a group of osmotic systems constructed in accordance with the teachings of U.S. Pat. No. 3,916,899, each containing 500 mg of acetazolamide.
Figure 3:
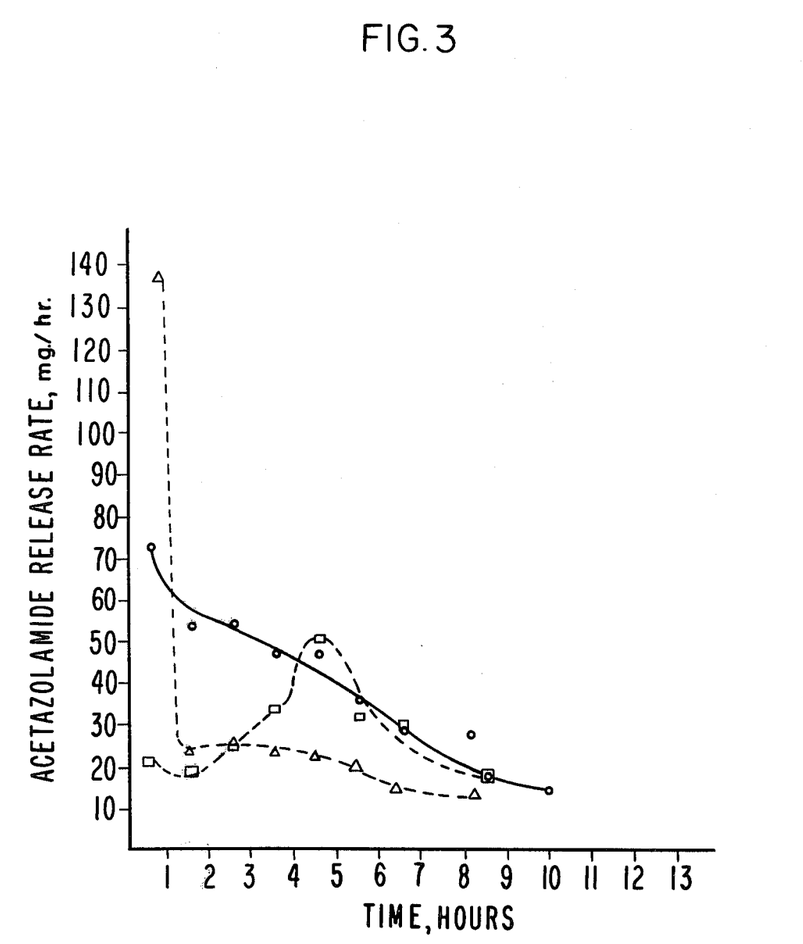
FIG. 3 illustrates the rate of release for three of the prior art non-osmotic sustained release rate forms each containing 500 mg of acetazolamide.

The invention's controlled and continuous rate of release of acetazolamide from an osmotic system is manufactured according to the specification and claims of U.S. Pat. Nos. 3,854,770 and 3,916,899. The rate of release for the non-osmotic prior art sustained released dose, is shown in FIG. 3. The prior art 500 mg dose released by the osmotic device of U.S. Pat. No. 3,916,899 and made herein for comparative evaluation is recorded in FIG. 1. FIG. 1 records the average rate of release for a group of osmotic systems each containing 500 mg of acetazolamide. In FIG. 1, the time in hours the system releases acetazolamide is plotted on the abscissa, the ordinate represents the amount released, the vertical bars represent variations from the means, and the circles represent the average amount released for 10 systems. The system administers acetazolamide at a zero order rate of 47 mg per hour over a zero order time period of from greater than 0 hours up to 7 hours. The system exhibited a standard deviation of ±10.6%, and it had a 4 mil thick wall made of cellulose acetate having an acetyl content of 32%. The passageway of the system had a diameter of 5.1 mils.

Figure 2:
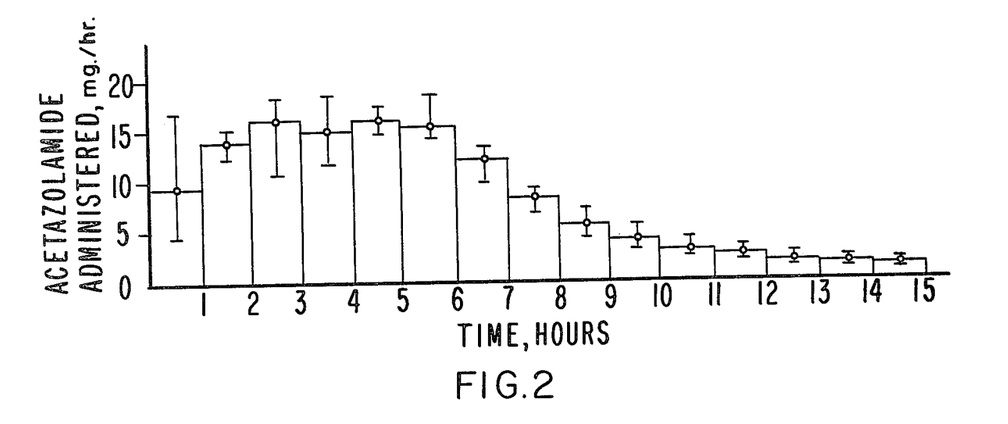
FIG. 2 illustrates the average rate of release for ten osmotic delivery systems in accordance with the present invention, each system containing 125 mg of acetazolamide as acetazolamide disodium.

The rate of release for an osmotic system comprising a semipermeable membrane formed of cellulose acetate surrounding a compartment containing sodium acetazolamide with a passageway through the membrane, as used for the purpose of the instant study is recorded in FIG. 2. The therapeutic program of the invention is presently carried out by using an osmotic device with a semipermeable wall comprising about 58 to 62% cellulose acetate having an acetyl content of 31 to 33%, about 30 to 34% cellulose acetate having an acetyl content of 39 to 40%, and about 7 to 9% polyethylene glycol, with the device housing up to 250 mg of acetazolamide which is released at a rate up to 20 mg/hr while lowering the intraocular pressure to a normal range. More specifically, the osmotic device comprises a water including body fluid, semipermeable membrane consisting of 60% cellulose acetate having an acetyl content of 32%; 32% cellulose acetate having an acetyl content of 39.8%, and 8% polyethylene glycol 400. The semipermeable membrane for an osmotic system embraced by these latter percentages expressed as weight are represented by 12.0 mg of cellulose acetate having an acetyl content of 32%, 6.4 mg of cellulose acetate having an acetyl content of 39.8% and 1.6 mg of polyethylene glycol 400. The compartment housed 170 mg of disodium acetazolamide equivalent to 125 mg of acetazolamide, 8.5 mg of polyvinyl pyrrolidone, and 1.78 mg of magnesium stearate. Osmotic delivery systems housing 250 mg of acetazolamide are structured and made in a similar manner. The osmotic devices were made according to the procedures described in the patents listed above. FIG. 2 records the average rate of release for 10 osmotic delivery systems each containing 125 mg of acetazolamide present in the device as acetazolamide disodium. In FIG. 2, the time in hours the system releases acetazolamide is plotted on the abscissa, the ordinate represents the amount released, the vertical bars represent actual variations from the means, and the circles represent the average amount released for the 10 samples. The sampling intervals in FIG. 2 were an hour apart and measured at 27° C. in either simulated gastric fluid or simulated intestinal fluid. The first two hourly samples were in gastric fluid and the next 3 to 15 hourly samples were measured in intestinal fluid.

The rate of release for three of the prior art non-osmotic sustained release rate forms each containing acetazolamide were measured in three different media and the results recorded in FIG. 3. The sustained release form is disclosed in *Physician Desk Reference.* In FIG. 3, the line having interlinear triangles represents a sustained release form containing 500 mg of acetazolamide, releasing it in simulated artificial gastric fluid adjusted to a pH of 1.3. This form exhibits during its initial 1½ hours in the juice an exponential rate of decay from 140 mg to 25 mg, then over the next 3½ hours it exhibited a variable rate of release of from 28 to 20 mg per hours, and for the next three hours it had a declining rate of release of 22 to 17 mg per hour. The form represented by the triangle does not lead to a zero order rate of release. In FIG. 3, the sustained release form identified by a line having interlinear circles, also contains 500 mg of acetazolamide but releasing it in simulated artificial intestinal fluid adjusted to pH 7.5. This form exhibited a quasi-exponential rate of decay from 72 mg to 20 mg per hour over an 8 hour period; this form, like the earlier described form, does not lead to a zero order rate of release. In FIG. 3, the line having interlinear squares represents a sustained release form containing 500 mg of acetazolamide with release occurring in artificial intestinal fluid adjusted to pH 7.0. This form during its first 2½ hours of release exhibited a rate of release of about 21 mg per hour, followed by an unpredictable increased rate of release up to 50 mg per hour over the next 1½ hours, with a decline to 33 mg per hour over the next 1½ hours. Finally, the form had a further decay in release from 33 to 18 mg per hour over the next 3 hours. This form gives a variable, non-zero order rate of release. Thus, FIG. 3 shows the prior art dosage forms do not lend themselves to controlled, non-changing zero order release. The figures also show that the release changes with the pH of the environment and in these states it is always larger over time than the release of this invention.

Figure 4:
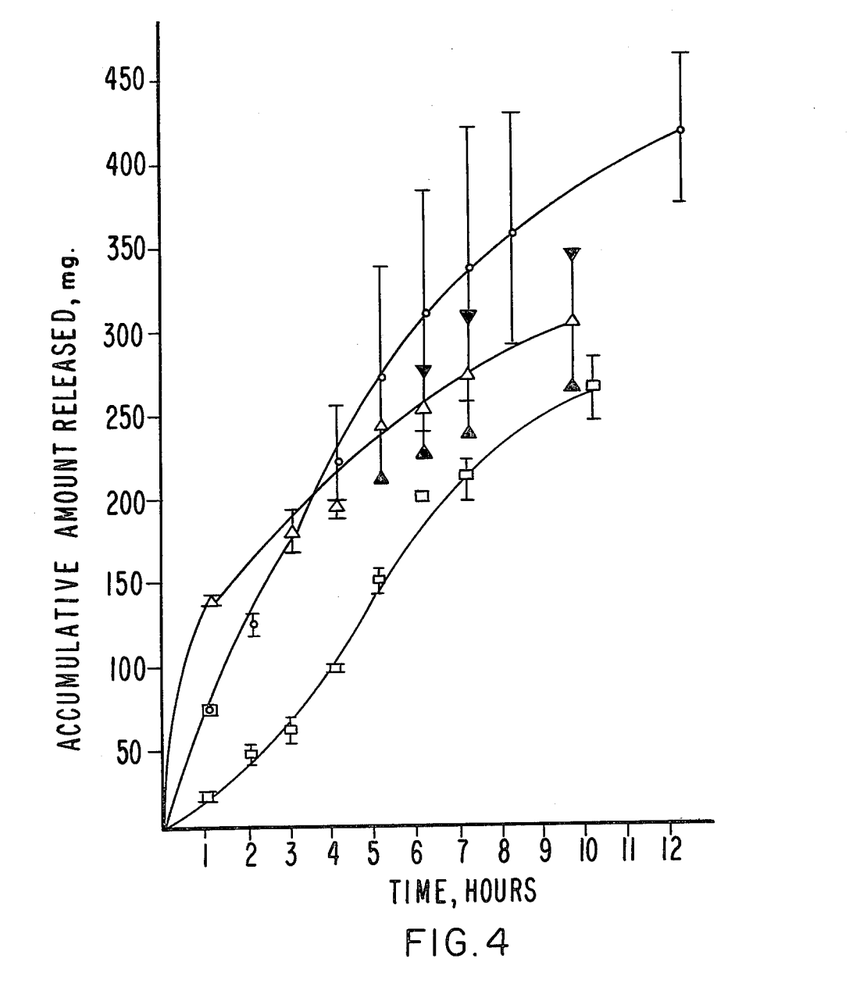
FIG. 4 illustrates the accumulative amount of acetazolamide released for six sustained release prior art forms over a period of up to 12 hours.

In FIG. 4, the accumulative amount of acetazolamide released for six sustained release prior art forms is plotted aginst time with the abscissa indicating time and the ordinate the accumulative amount released in mg. In FIG. 4, the line having interlinear circles represents measurements made in artificial intestinal fluid adjusted to pH 7.5, the line with interlinear triangles represents measurements made in artificial gastric fluid adjusted to pH 1.2, and the line having interlinear squares represents measurements made in intestinal fluid adjusted to pH 7.0. Also, in FIG. 4, the vertical bars represent actual variations from the means, and the circle, triangle or square datum points represent the average of two measurements.

Figure 5:
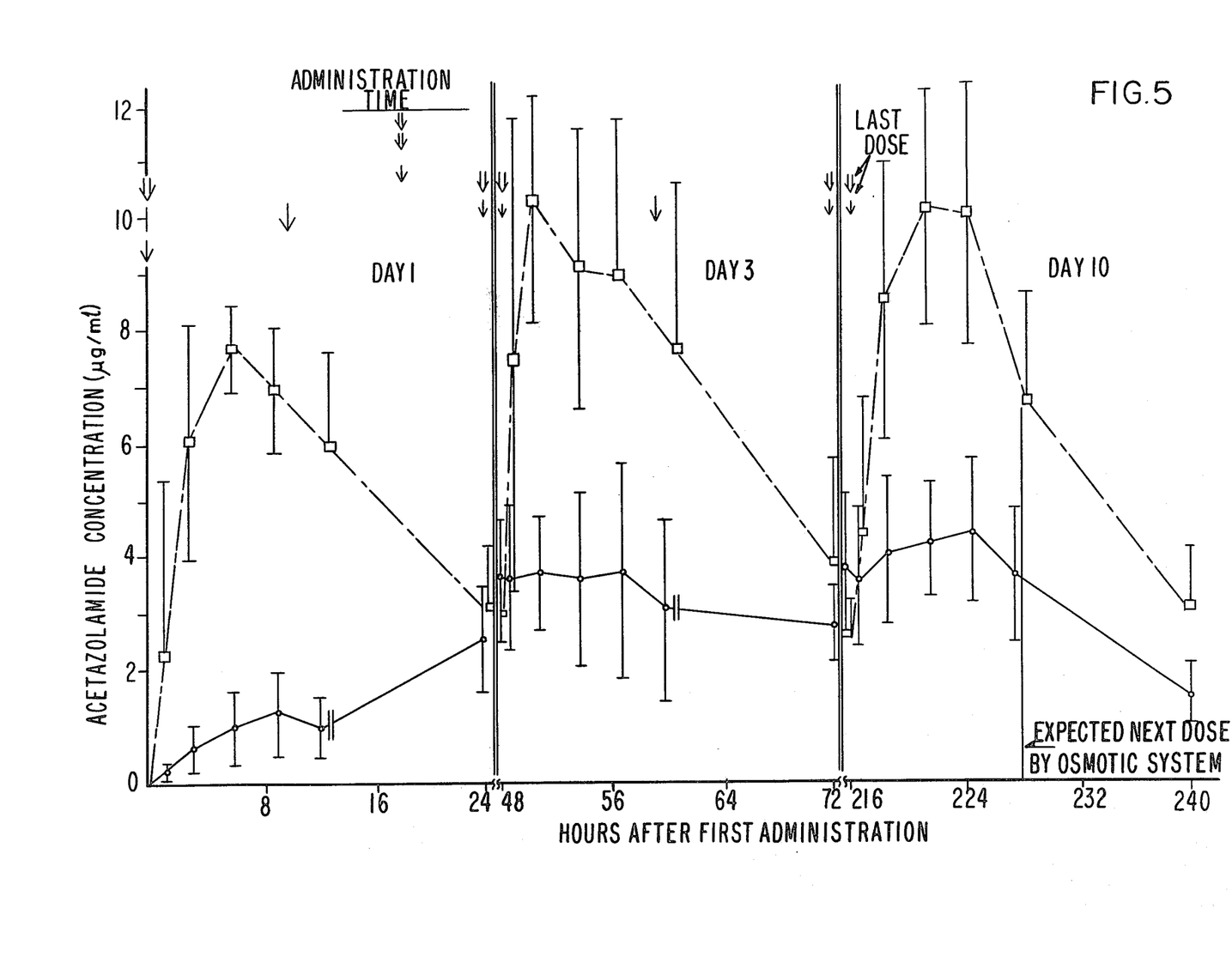
FIG. 5 illustrates a comparison between the administration of acetazolamide in accordance with the present invention and in accordance with the prior art with the acetazolamide concentration in blood plasma being recorded over a period of 12 days.
Figure 6:
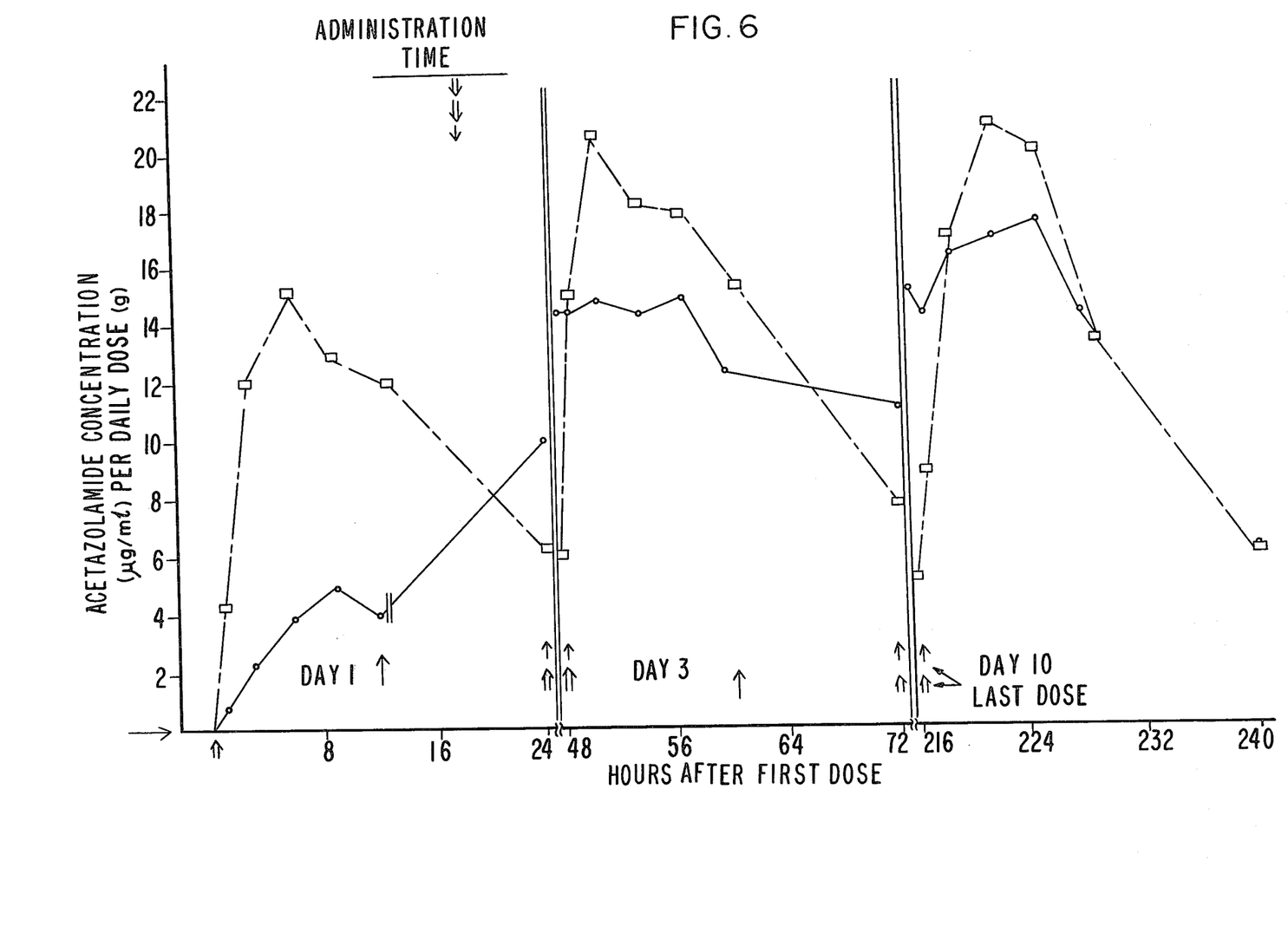
FIG. 6 illustrates the data of FIG. 5 normalized to daily dose.
Figure 7:
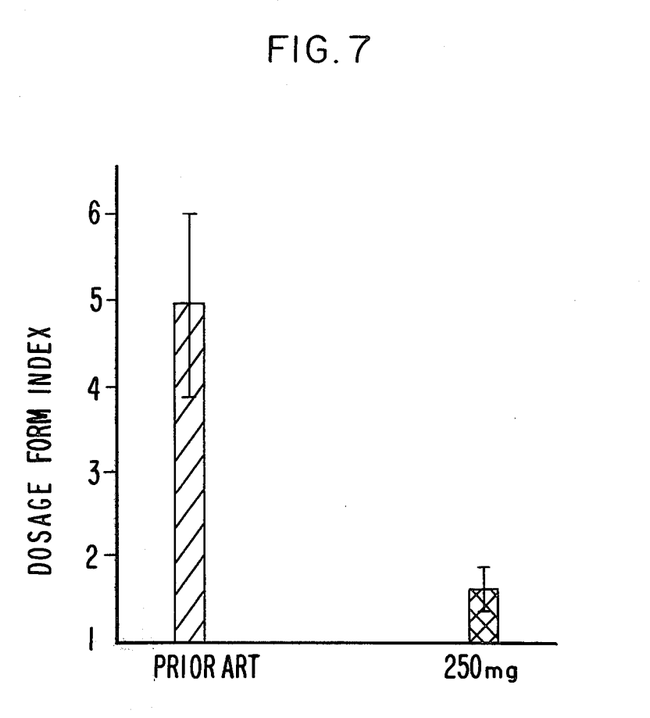
FIG. 7 illustrates the dosage form index of the prior art compared to the present invention.

In FIGS. 5, 6, and 7, the results obtained from a controlled study comprising orally administering acetazolamide according to this invention by an osmotic device are compared and plotted against the results obtained by orally administering acetazolamide using a prior art sustained release form. The purpose of the study was to measure the plasma levels obtained by administering acetazolamide using the two different types of administration, to a group of normal, human adult volunteers. The osmotic system used to administer sodium acetazolamide contained 125 mg of acetazolamide, expressed as acetazolamide, and it had a rate of release to 15 mg/hr. The sustained release form used to administer acetazolamide contained 500 mg of acetazolamide, and it delivered the drug in a quasi-exponential declining rate as described in FIGS. 3 and 4. The osmotic system was administered twice a day for a daily dose of 250 mg of acetazolamide, and the sustained release form was administered once a day for a daily dose of 500 mg of acetazolamide. The study was performed using conventional cross-over techniques. The osmotic system was administered to five of eight volunteers, and the sustained release form was administered to eight volunteers. Both the osmotic system and the sustained release forms were administered for 10 days to achieve a steady state that was verified by sampling the blood at frequent intervals during days 1, 3 and 10.

The average plasma level for the eight humans administered acetazolamide by the sustained release form is plotted in FIG. 5, indicated by the line with the squares. The average plasma level for the five humans administered acetazolamide by the osmotic system is plotted in FIG. 5, indicated by the line with the circles. The numbers on the ordinate represent the acetazolamide concentration in the plasma, and the numbers on the abscissa indicate the time after administration the concentration was measured in the plasma. FIG. 5 indicates the substantially average plasma concentrations expressed as $\mu g/ml$ obtained with the osmotic system and the sustained release form, with this invention producing an average plasma concentration of greater than zero up to 6 $\mu g/ml$, and the sustained release form producing an average plasma concentration of greater than 7 to 11 $\mu g/ml$. This is further illustrated in FIG. 6 where the data of FIG. 5 are normalized to the daily dose. In FIG. 6, the average normalized plasma concentration is expressed on the ordinate as $\mu g/ml/$daily dose (g), and the numbers on the abscissa represent determinations made at certain hours after the first dose. The broken line with the squares represents the sustained release form, and the line with the circles represents the osmotic system. The results indicate the acetazolamide concentration in g/ml per daily dose is more constant for this invention than for the results obtained with the prior art.

FIG. 7 represents the plasma fluctuations for the osmotic systems and sustained release forms, which is expressed as the maximum to minimum ratio of the plasma level encountered in a unit dosing time on repetitive administration. The average of this ratio, as listed on the ordinate, over subject and time, is defined as the dosage-form index (DI). In FIG. 7, the phrase "prior art" along the abscissa indicates the dosage form index for the sustained release form, and "250 mg" indicates the dosage form index for the osmotic system. In the figure, the dosage form index for the sustained release form is the average ratio for the maximum to minimum acetazolamide plasma concentration levels encountered in a 24 hour dosing period during days 3 and 10 average over all subjects. The dosage form index for the 250 mg osmotic system is the ratio of maximum to minimum plasma levels encountered in the 13 hours steady state interval on days 2 and 10 averaged over all subjects. In FIG. 7, the slanted lines represent the prior art, and the cross lines represent the 250 mg system. In FIG. 7, the method of this invention exhibited an unexpected smaller dosage form index which, by convention, means less plasma fluctuation and has further been related to less side effects. The dosage form index for this invention is 1.6, while the prior art is five. The above studies as represented by FIGS. 5, 6, and 7, are seen as indicating unobvious and unexpected superior plasma levels for the method of this invention. This is advantageous for the management of intraocular pressure with less side effects, particularly as associated with glaucoma.

The clinical efficacy of the methods and profile of the invention was demonstrated by the studies reported below. The acetazolamide was orally administered to a group of 8 adult men and women patients who were selected based on the following criteria. The patients must have an untreated intraocular pressure greater than 28 mm Hg. The patients must not have received any epinephrine for at least one month prior to study. The patients must be responsive to acetazolamide as evident by an intraocular pressure lowered to 22 mm Hg with a minimum decrease of 6 mm Hg from the untreated level by administering orally 250 mg of acetazolamide at least 72 hours prior to the study. The patients selected for the study did not have any other illness and they were not taking any other drug which must adversely influence the study and its results. The study was performed using conventional cross-over, double-blind techniques, and the placebos used were made of lactose. The dosage program of the study obtained with the method of the invention and the results obtained for the method were compared with the results obtained by administering the above described commercially available containing acetazolamide.

The drug was administered to each of the 8 patients according to four treatment plans. Each patient used one of the four treatment plans for a five day period followed by another treatment plan until all the plans were administered to each patient during the four consecutive weeks of the study. The four plans comprised (a) orally administering one osmotic delivery system containing 125 mg of acetazolamide that is releasing at a rate of 15 mg per hour with the system administered twice a day for a daily dose of 250 mg (b) orally administering two osmotic systems at one administration with each containing 125 mg of acetazolamide and having an initial rate release of 15 mg per hour with the systems administered twice a day for a daily dose of 500 mg A, (c) orally administering one 250 mg tablet twice a day for a daily dose of 500 mg of acetazolamide, and (d) orally administering one placebo twice a day. The order each patient was administered the four plans was randomly determined, with each patient receiving one plan twice daily starting on day 1 at 8:00 AM and ending on the 5th day at 8:00 AM for a total of 9 administrated tablets, or placebos for each patient.

Each patient's intraocular pressure was measured with a standard non-contacting tonometer with three measurements made and averaged at one time. The tonometer is commercially available from the American Optical Company. Each patient's blood was drawn, and the amount of acetazolamide measured in the plasma according to the procedure disclosed in *J. Pharm. Sci.*, Volume 64, pages 402 to 404, 1975. The side effects or reactions were evaluated by giving each patient a card listing the side effects, having the patient check the side effects experienced since the last observation and classify their intensity as mild, moderate, or severe.

The results of the study were analyzed, using analysis of variance, sample averages, and standard deviations were calculated for intraocular pressure and the amount of acetazolamide measured in the plasma. The data were analyzed statistically to determine significant differences among the plans and for the measured parameters. The lowering in intraocular pressure, the incidence and severity of side effects were plotted as a function of acetazolamide plasma concentration for each plan. The results of the study are recorded in the accompanying figures.

Figure 8:
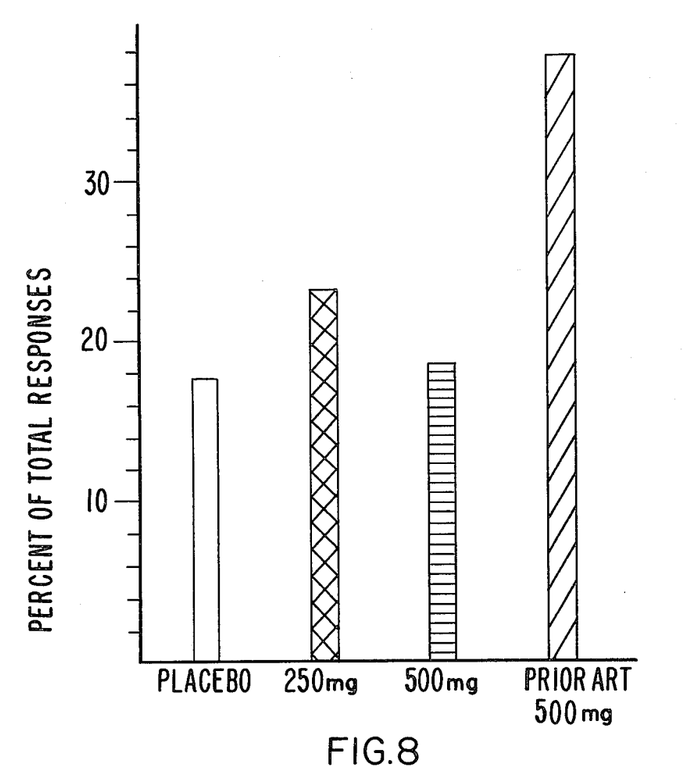
FIG. 8 illustrates the incidence of all side effects measured upon administration of a placebo, acetazolamide in accordance with the present invention and acetazolamide in accordance with the prior art.

In FIG. 8, the sum of all incidence of side effects measured is reported for the study. In FIG. 8, the numbers on the ordinate are the percent of total response as recorded by the patient on the evaluation card as mild, moderate or severe. The numbers on the abscissa indicate the total amount of acetazolamide administered to the method of the invention twice daily, the column with horizontal lines indicates administration twice daily of two zero order systems each containing 125 mg of azetazolamide, and the column with the slanted lines indicates the administration 250 mg of acetazolamide twice daily using the prior art tablet method of administration. The FIG. 8 shows a 47% decrease in all incidence of side effects for the invention compared to the prior art. In all of the side effect studies, the percentage reduction of side effects is based on comparison of the prior art with equal doses of both dosage forms.

Figure 9:
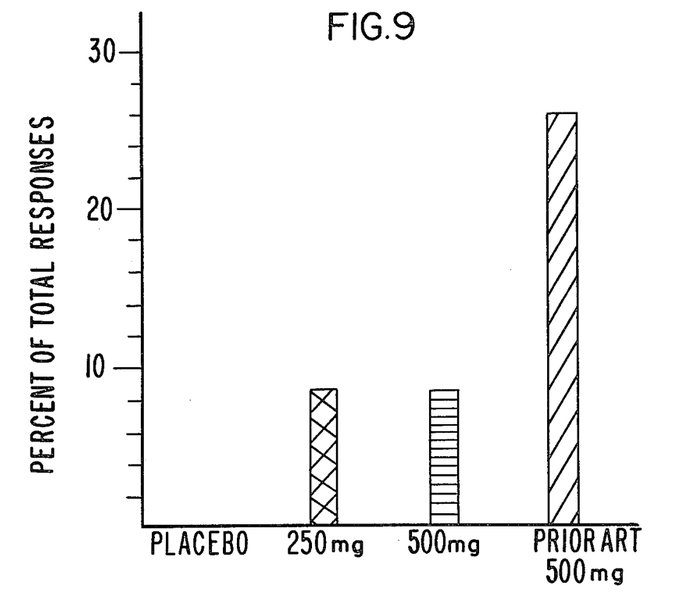
FIG. 9 illustrates the incidence of drowsiness measured upon administration of a placebo, acetazolamide in accordance with the present invention and acetazolamide in accordance with the prior art.
Figure 10:
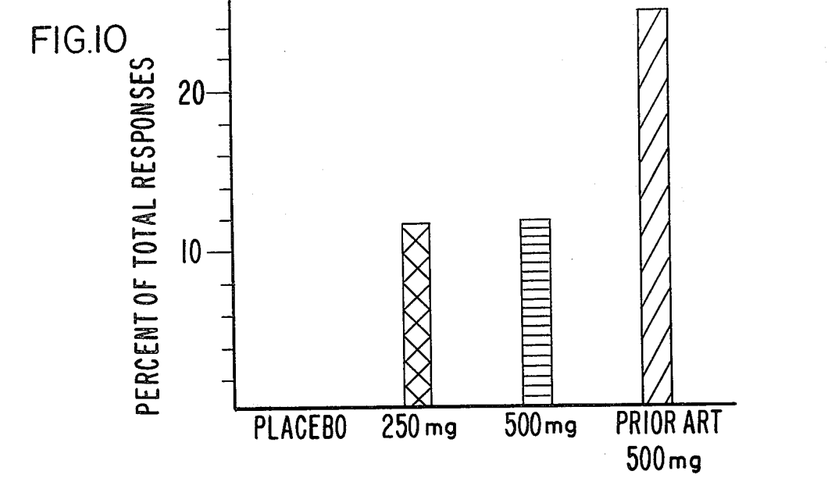
FIGS. 10 and 11 illustrate the incidence of paresthesia measured upon administration of a placebo, acetazolamide in accordance with the present invention and acetazolamide in accordance with the prior art.
Figure 11:
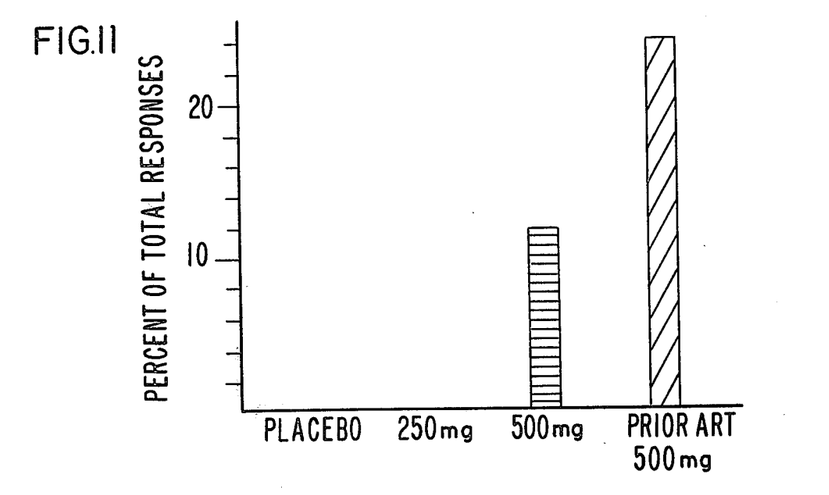
Figure 12:
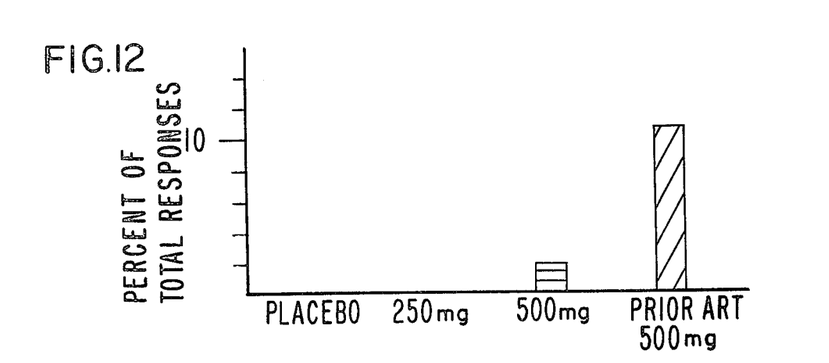
FIG. 12 illustrates the incidence of confusion measured upon administration of a placebo, acetazolamide in accordance with the present invention and acetazolamide in accordance with the prior art.

The results of FIG. 9 indicate an unexpected 69% lessening in side effects for the method of this invention compared with the prior art. In FIG. 9, the incidence of drowsiness is recorded for the method of the study compared with the prior art tablet method of administration. The description along the ordinate, the markings in the columns, and the numbers along the abscissa are set forth in FIG. 9. The results of FIG. 10 indicated 52% lessening of the incidence of paresthesia for the method of this invention. In FIG. 10 the incidence of paresthesia as felt by tingling of the hands for the method of the study is recorded and compared with the tablets. The legends for ordinate, the abscissa and the columns are as described for FIG. 8. In FIG. 11, the incidence of parethesia as felt by tingling feet for the method of the study is recorded and compared with the method of administration of sustained release mode of administration. The legend for the ordinate, the abscissa and the columns are as described for FIG. 8. The results of FIG. 11 indicated a decrease of about 48% in the incidence of tingling feet for the method of the study as recorded and compared with the tablet dosage method. In FIG. 12, the incidence of confusion for the method of the study is recorded and compared with the tablet method of use. The legends along the ordinate, along the abscissa and for the column are as described for FIG. 8. The results of FIG. 12 indicated a decrease of about 82% in the incidence of confusion for the method of the study compared with the sustained release method.

Figure 13:
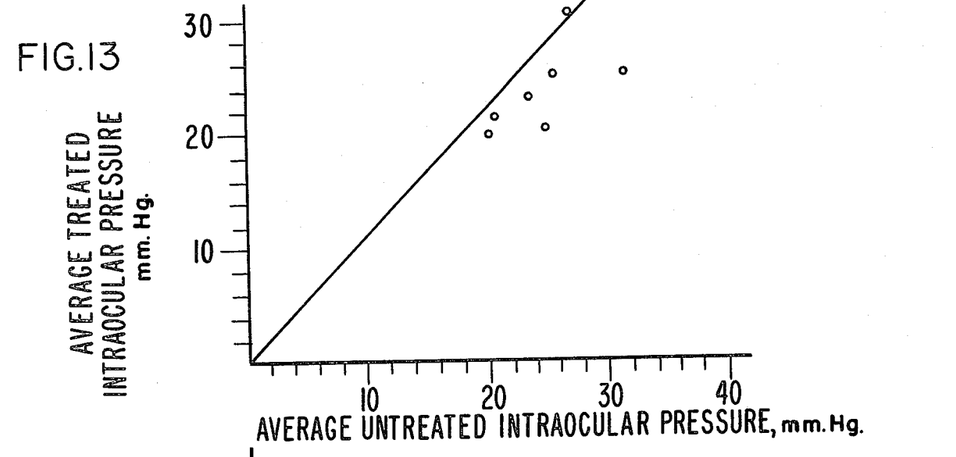
FIGS. 13, 14 and 15 illustrate the average intraocular pressure for patients administered various forms of acetazolamide compared with the average intraocular pressure for the same group of patients receiving a placebo.
Figure 14:
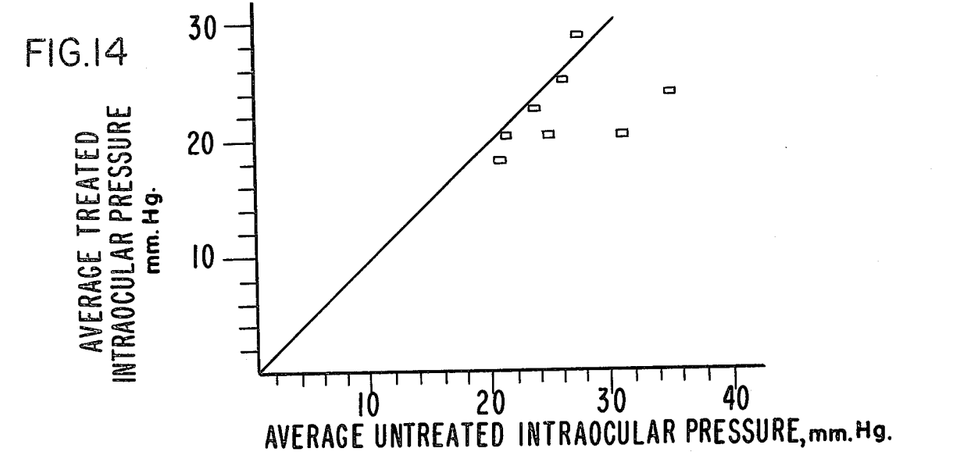
Figure 15:
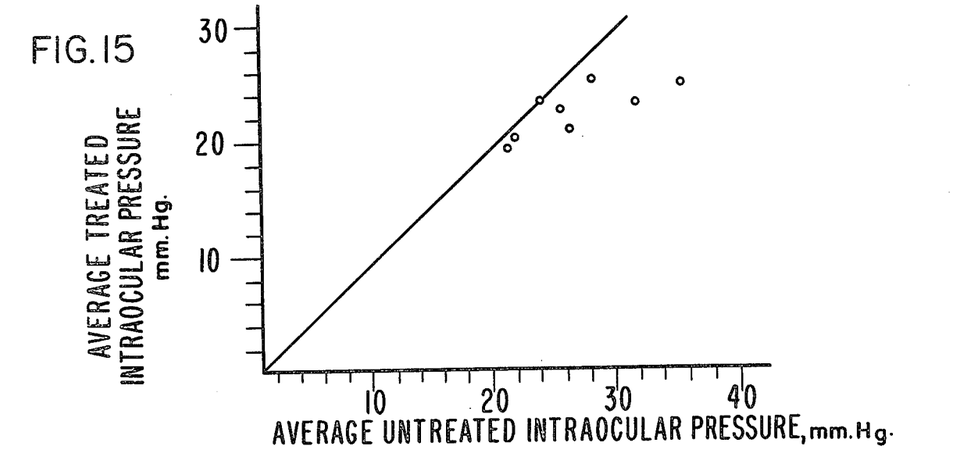

In FIG. 13, the average intraocular pressure for patients administered 125 mg of acetazolamide twice a day is recorded and compared with the average intraocular pressure for the same group of patients receiving the placebo. The treated patients were administered 125 mg of acetazolamide twice a day with the drug administered according to the invention. In FIG. 13, the number along the ordinate indicates the average intraocular pressure for the patients treated with acetazolamide, the numbers along the abscissa indicate the average intraocular pressure for the same patients untreated, and each dot indicates the average of 5 measurements for one patient. The measured results indicated this method of administration lowered intraocular pressure in patients administered acetazolamide. FIG. 14 is similar to FIG. 13 with all conditions and legends as described except in this figure the treated patients now were administered two osmotic systems each containing 125 mg of acetazolamide twice a day. Each square in FIG. 14 indicates the average measurement of intraocular pressure for one patient. The results of FIG. 14 indicated this method of administering acetazolamide lowered intraocular pressure in patients. FIG. 15 is similar to FIGS. 13 and 14 with all conditions and legends as described above, except in this figure the treated patients were administered one tablet containing 250 mg of acetazolamide twice a day. The circles are the average of five measurements for one patient.

Figure 16:
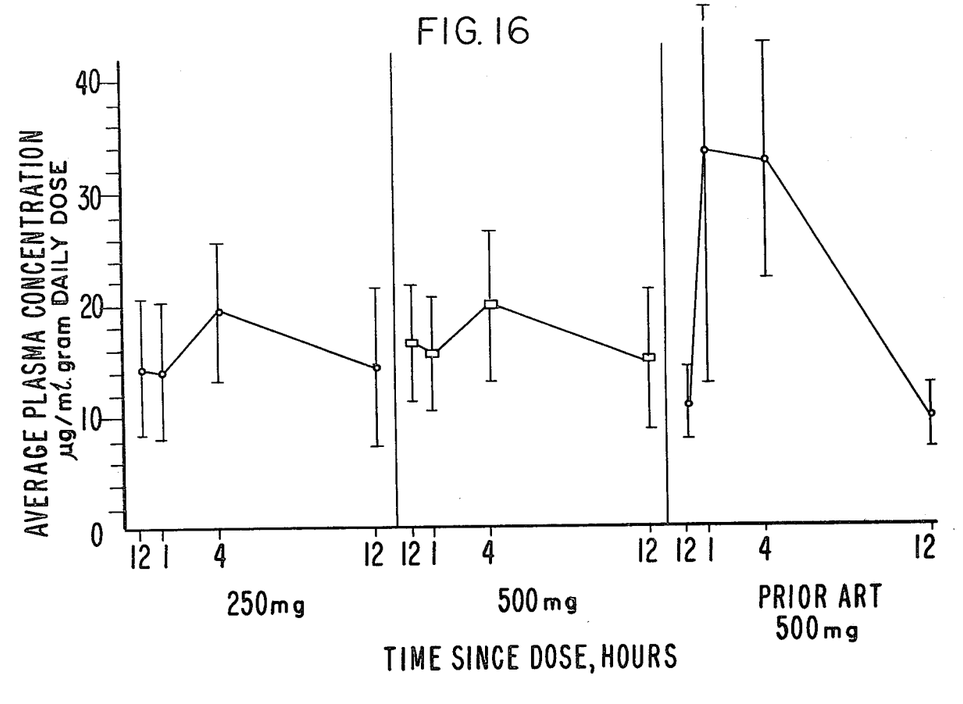
FIG. 16 illustrates the average, normalize acetazolamide plasma concentration at steady state of patients receiving an osmotic system at daily dosages of 200 and 500 mg and a prior art tablet form of 500 mg of acetazolamide.

In FIG. 16, the average, normalized acetazolamide plasma concentration at steady state of patients receiving an osmotic system containing 125 mg of acetazolamide administered twice a day for a daily dose of 250 mg, and for an osmotic system containing 125 mg of acetazolamide administered two at a time taken twice a day for a daily dose of 500 mg, is compared with the average, normalized acetazolamide plasma concentration at steady state obtained by administering a tablet form containing 250 mg of acetazolamide twice daily for a daily dose of 500 mg. The legend on the ordinate is the average plasma concentration in g/ml, normalized to a daily dose of 1 g. The normalized values are converted to the actual plasma concentrations as seen in FIG. 5 by multiplying the normalized value by the daily dose administered in each therapeutic regimen in g, as indicated beneath the abscissa in FIG. 16. The numbers on the abscissa are time passed since the acetazolamide was administered measured in hours, 250 mg indicate amounts given by the method of the invention, and the term "prior art" means a conventional 250 mg tablet form. The results of the study indicated a more steady state plasma level, of 14 to 20 g/ml normalized to a daily dose of 1 g for this invention, compared to a more variable 10 to 34 g/ml plasma level normalized to a daily dose of 1 g for the prior art, while the efficacy of both regimen is comparable as exemplified by FIGS. 13, 14 and 15.

Figure 17:
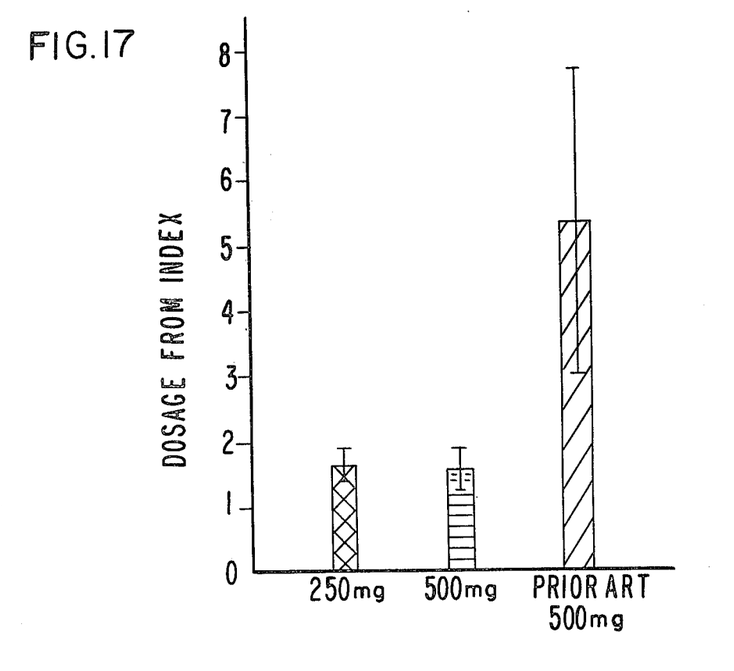
FIG. 17 illustrates a comparison of the dosage form index obtained with the present invention and in accordance with the prior art.

In FIG. 17, the average dosage form indexes obtained by studying all the patients expressed as their ratios of maximum to minimum acetazolamide plasma concentration during the inter-dose interval for the methods of the invention is recorded and compared with the prior art. The numbers along the ordinate are the dosage form index, and the numbers along the abscissa indicate the amount of acetazolamide administered daily. The column with crossed lines indicates 125 mg of acetazolamide administered by an osmotic system twice a day, the column with the horizontal lines indicates two osmotic systems each containing 125 mg of acetazolamide were administered twice a day, and the column with the slanted lines indicates the administration of 250 mg of acetazolamide twice daily in tablet form. The vertical bars with horizontal terminal lines are the standard deviation. The dosage form index as set forth in FIG. 17 is a function of the intrinsic pharmaco-kinetic properties of the drug, dosing interval and characteristics of the dosage form, and at equal dosing intervals different dosage forms can be compared. The drug delivery system with the lowest dosage index is unexpectedly therapeutically superior. The importance of dosage form index can be ascertained by reading the prior art. See *Physico-Chemical Aspects of Drug Actions,* Volume 7, Kruger-Thiemer, pages 63 to 112, 1965, published by Pergamon Press, N. Y.; and *Fundamentals of Clinical*

*Pharmacokinetics,* 1st Edition, by Wagner, published by Drug Intelligence Publications, Inc., Hamilton, Ill. The dosage form index is more than one-hundred percent less than the prior art.

Figure 18:
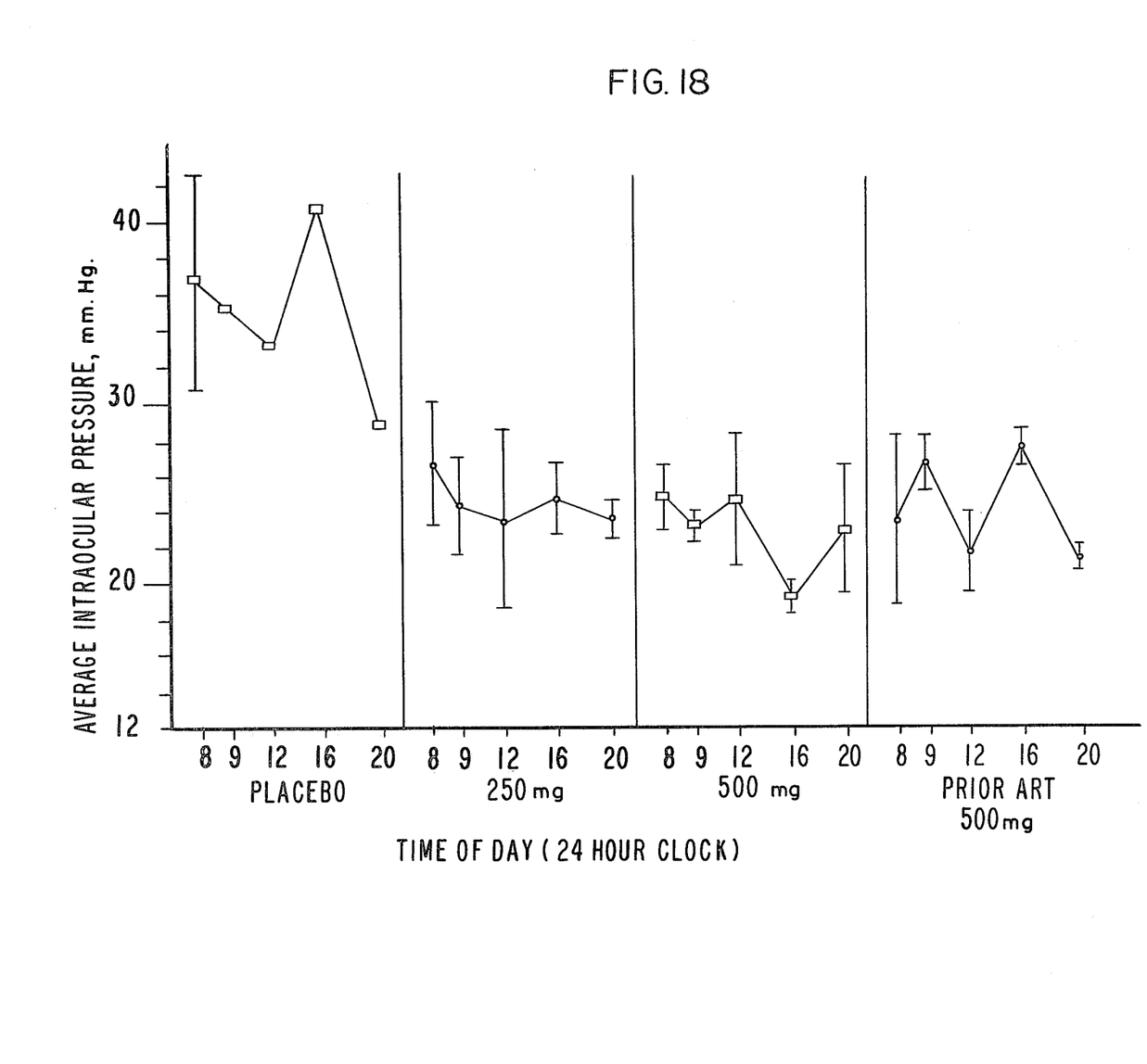
FIG. 18 illustrates the average intraocular pressure as a function of time for patients administered placebos, 250 and 500 mg of acetazolamide per day according to the present invention and 500 mg of acetazolamide per day in tablet form.

FIG. 18 is an average intraocular pressure as a function of time for a typical patient. The patient was administered placebos, 250 mg of acetazolamide per day, and 500 mg of acetazolamide per day according to the method of the invention. The patient was also administered 500 mg of acetazolamide in tablet form. In FIG. 18, the numbers on the abscissa indicate the time of day the intraocular pressure was measured. The numbers along the abscissa, 250 and 500 appearing consecutively from the left, indicate milligrams of acetazolamide administered according to the method of the study. Also in the figure, the 500 mg at the extreme right indicates acetazolamide administered in tablet form as prior art method. The numbers along the ordinate are the average intraocular pressure measured in mm Hg. The results obtained by this invention indicates an average lowering of the intraocular pressure of about 15 mm Hg for this study.

The data presented shows that the continuous, controlled delivery of acetazolamide according to the methods and substantially zero order rates of release of this invention to warm blooded animals lessens the incidence of side effects and lowers intraocular pressure and is useful for treating glaucoma. Additionally, the data shows that plasma levels are maintained in a steady state and at levels lower than the peak levels obtained by the method of administration of the prior art. The data presented herein demonstrates that the occurrence of unwanted side effects are significantly lessened thereby making the methods of the invention a valuable contribution to medicine. The results of this invention do not appear to be anticipated in view of the prior art as reported in *Am. J. Ophthal.,* Volume 55, pages 323 to 327, 1963. In the reported study it was shown that 250 mg tablets administered four times daily exhibited an increase in side effects when compared against a sustained release dosage form containing 500 mg administered once a day. In the present study, it was shown that using the method of this invention comprising controlled, continuous zero order release, the dosage form index was reduced to 1.5 compared to the sustained dosage form of 5, and that the dosage form index for the tablet is also 5, or the same as the sustained dosage form. Also, the present study demonstrated that a reduction of plasma level fluctuations obtained by this invention expressed as a reduction in dosage form index resulted in a lessening in side effects.

The statistically significant therapeutic program of the invention embraces a substantially constant drug input rate to the systemic circulation in the range of greater than zero up to 20 mg/hr, while producing a constant, non-spiked plasma concentration in the range of greater than zero up to 10 g/ml. The plasma concentration is substantially constant as exemplified by the low dosage form index compared to the dosage form index produced by the prior art tablets. The results of this invention also produce a substantial reduction in side effects when equal amount of drug is administered while also producing an equal efficacy lowering of the intraocular pressure.

While certain specific considerations have been disclosed and discussed herein, such have been offered to exemplify the present invention, and they should not be considered as limiting the scope and nature of the invention.

We claim:

1. In a method for treating ocular hypertension in a warm-blooded animal responsive to acetazolamide and having ocular hypertension, the improvement consisting of orally administering to the animal an osmotic dosage formulation consisting of a wall of semipermeable cellulose acetate surrounding a compartment containing up to 250 mg of acetazolamide, which is released through a passageway in the wall to the animal in a controlled, and continuous rate, and in a therapeutically effective amount up to 20 milligrams per hour over a prolonged period up to 12 hours to produce effective blood levels for lowering intraocular pressure within the average normal range, said method of acetazolamide administration occurring independent of the pH of the animal, producing a hypotensive effect, a blood plasma acetazolamide concentration that is in a steady, substantially constant state and characterized by a low plasma dosage form index of less than 2.5 as exemplified by the ratio of the maximum to minimum plasma concentration of the acetazolamide, said plasma concentration lower than the plasma level obtained by non-osmotic delivery of acetazolamide while concomitantly equally lowering the intraocular pressure and lessening the incidence of side effects of drowsiness, confusion and paresthesias associated with the administration of acetazolamide.

2. A method for treating ocular hypertension in a warm-blooded animal according to claim 1 wherein the treating of ocular hypertension consists in lowering the intraocular pressure associated with narrow-angle glaucoma, wide-angle glaucoma, and secondary glaucoma.

3. A method for treating ocular hypertension in a warm-blooded animal according to claim 1 wherein the plasma concentration of acetazolamide in the animal administered up to 20 milligrams per hour is up to 6 micrograms per milliter of plasma.

4. A method for treating ocular hypertension in a warm-blooded animal according to claim 1 wherein the method produces an intraocular pressure lowering of up to 15 mm Hg.

5. A method for treating ocular hypertension in a warm-blooded animal according to claim 1 wherein the wall of semipermeable cellulose acetate consists of 58 to 62% cellulose acetate having an acetyl content of 32%, and 30 to 34% cellulose acetate having an acetyl content of 39.8%.

6. A method for treating ocular hypertension in a warm-blooded animal according to claim 1 wherein the wall of semipermeable cellulose acetate contains from 7 to 9% polyethylene glycol.

7. An oral, osmotic delivery device containing acetazolamide, said device having a semipermeable wall consisting essentially of 58 to 65% cellulose acetate having an acetyl content of 31 to 33%, from 30 to 32% cellulose acetate having an acetyl content of 39 to 40%, and from 7 to 9% of polyethylene glycol, said device having a passageway through said wall, the device being constructed so as to release the acetazolamide in a controlled, continuous rate and in a therapeutically effective amount up to 20 milligrams per hour to produce effective blood levels for lowering intraocular pressure within the average normal range and to obtain a low plasma dosage form index of less than 2.5 as exemplified by the ratio of the maximum to minimum plasma concentration of the acetazolamide.

8. The oral, osmotic delivery device according to claim 7 wherein the 58 to 65% cellulose acetate has an acetyl content of 32%, and the 30 to 32% cellulose acetate has an acetyl content of 39.8%.

* * * * *